United States Patent [19]

Braestrup et al.

[11] Patent Number: 4,507,313
[45] Date of Patent: Mar. 26, 1985

[54] OXADIAZOLYL-IMIDAZO-[1,4]BENZODIAZEPINES AND THEIR USE IN TREATMENT OF DISEASES OF THE CENTRAL NERVOUS SYSTEM

[75] Inventors: Claus T. Braestrup, Roskilde; Joergen A. Christensen, Virum; Mogens Engelstoft, Vaerloese; Frank Waetjen, Bagsvord, all of Denmark

[73] Assignee: A/S Ferrosan, Soborg, Denmark

[21] Appl. No.: 551,818

[22] Filed: Nov. 15, 1983

[30] Foreign Application Priority Data

Nov. 15, 1982 [DK] Denmark ............................. 5102/82

[51] Int. Cl.³ ................. A61K 31/555; C07D 521/000
[52] U.S. Cl. ............................. 514/220; 260/239.3 P; 548/131; 548/336
[58] Field of Search ................. 260/239.3 T; 548/131, 548/336; 424/272, 273 R

[56] References Cited

U.S. PATENT DOCUMENTS 4,386,028  5/1983  Hunkeler et al. ............ 260/239.3 T Primary Examiner—Robert T. Bond
Attorney, Agent, or Firm—Millen & White

[57] ABSTRACT

New oxadiazolyl-imidazo-[1,4]benzodiazepine derivatives having benzodiazepine receptor activity have the formula

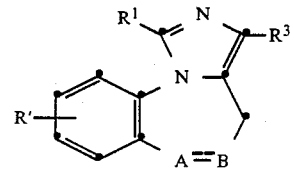

$R'$ is hydrogen, chlorine, fluorine or nitro in the 7- or 8-position,
$R^1$ is hydrogen or lower alkyl of up to 3 carbon atoms,
$R^3$ is the oxadiazolyl grouping of the formula

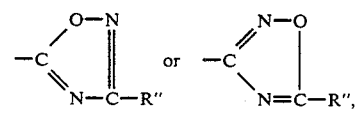

wherein $R''$ is lower alkyl with up to 3 carbon atoms and A≐B is a grouping of the formula

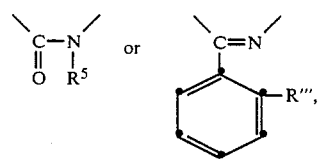

wherein $R^5$ is hydrogen or methyl and $R'''$ is hydrogen or chlorine.

The compounds possess valuable pharmacological properties. In particular, they act on the central nervous system and are suitable for use in psychopharmaceutical preparations.

16 Claims, No Drawings

OXADIAZOLYL-IMIDAZO-[1,4]BENZODIAZEPINES AND THEIR USE IN TREATMENT OF DISEASES OF THE CENTRAL NERVOUS SYSTEM

This invention relates to new oxadiazolylbenzodiazepine derivatives which bind to benzodiazepine receptors.

SUMMARY OF THE INVENTION

It is an object of this invention to provide new compounds having the activity of binding to benzodiazepine receptors.

Upon further study of the specification and appended claims, further objects and advantages of this invention will become apparent to those skilled in the art.

These objects have been achieved by providing oxadiazolyl-imidazo-[1,4]benzodiazepine derivatives of formula I

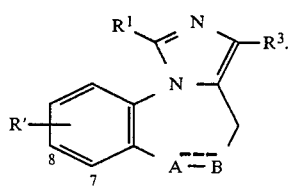

wherein,
$R'$ is hydrogen, or chlorine, fluorine or nitro in the 7- or 8-position,
$R^1$ is hydrogen or lower alkyl of up to 3 carbon atoms,
$R^3$ is an oxadiazolyl of the formula

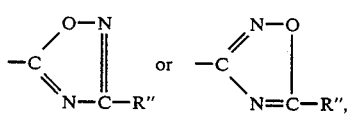

$R''$ is lower alkyl of up to 3 carbon atoms,
$A \mathrel{\substack{=\\=}} B$ is a grouping of the formula

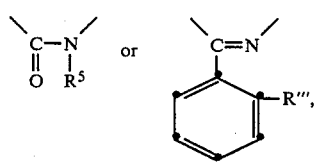

$R^5$ is hydrogen or methyl, and
$R'''$ is hydrogen or chlorine.

DETAILED DISCUSSION

The novel compounds of this invention possess valuable pharmacological properties, acting particularly on the central nervous system. They are suitable for use in psychopharmaceutical preparations.

European patent application No. 0054507 discloses a number of β-carboline derivatives which bind strongly to the so-called benzodiazepine receptors (cf. Squires, R. F. and Braestrup, C., Nature (London) 266 (1977) 734). Some of the compounds of this invention have a 3-(5-oxadiazole)-β-carboline structure.

A detailed study of the 3-(5-oxadiazole)-β-carbolines of this invention has revealed a surprisingly stronger binding to the benzodiazepine receptors than analogous 3-substituted-β-carbolines. Furthermore, it has been found that a corresponding increase in binding strength is also obtained with the other oxadiazolylbenzodiazepine compounds of this invention which are derivatives of other benzodiazepine receptor active compounds.

Lower alkyl herein includes methyl, ethyl, n-propyl and isopropyl.

The compounds of this invention may conventionally be prepared, e.g., (1) by reacting a reactive derivative of a compound of formula II

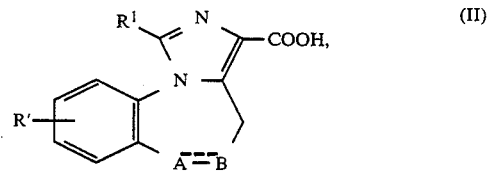

wherein $A \mathrel{\substack{=\\=}} B$, $R^1$ and $R'$ are as defined above, with a compound of the formula

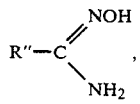

wherein $R''$ is as defined above, to form a compound of formula I wherein $R^3$ is

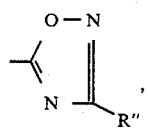

wherein $R''$ is as defined above, or (2) by reacting a compound of formula III

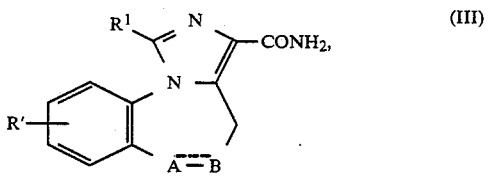

wherein $A \mathrel{\substack{=\\=}} B$, $R^1$ and $R'$ are as defined above, with a compound of the formula $R''\text{-}C(OMe)_2NMe_2$, wherein $R''$ is as defined above, to form a compound having formula IV

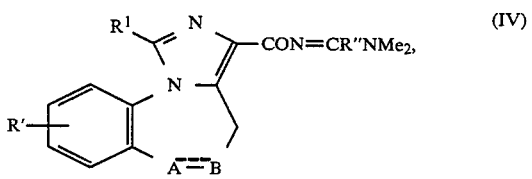

wherein $A \mathrel{\substack{=\\=}} B$, $R'$, $R''$ and $R^1$ are as defined above, and reacting the compound thus obtained with $NH_2OH$ or an aminating agent, e.g., O(mesitylene sulfonyl)hydroxylamine, to form a compound of formula I, wherein $R^3$ is

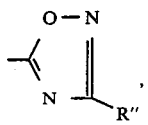

or (3) by reacting a compound of formula V

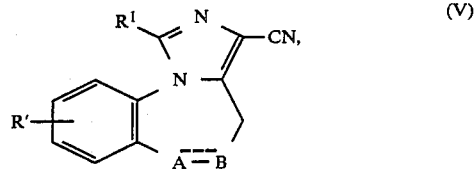

wherein A ≈≈≈≈ B, R¹ and R' are as defined above with NH₂OH to form a compound of formula VI

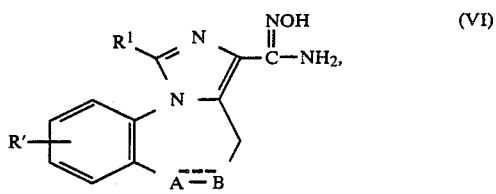

wherein A ≈≈≈ B, R¹ and R' are as defined above, and reacting the compound thus obtained with (R"CO)₂O, wherein R" is as defined above, to form a compound of formula I, wherein R³ is

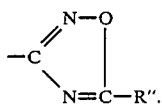

All reactions are conventional and can be carried out under the usual conditions. For example, reaction 1 is usually carried out with a temperature of 20°–150° C., a reaction time of 1–5 hours, a ratio of the amount of imidazolide of compound of formula II to its coreactant of 1:3, e.g., in a mixture of THF, DMF, toluene or xylene. The first step of reaction 2 is usually carried out with a temperature of 90°–120° C., a reaction time of 1–4 hours, a ratio of the amount of compound of the formula III to its coreactant of 1:3, e.g., using the coreactant as solvent. The second step of reaction 2 is usually carried out with a temperature of 70°–110° C., a reaction time of 1–3 hours, a ratio of the amount of compound of step 1 to its coreactant of 1:1.2, in a solvent, e.g., aqueous sodium hydroxide, acetic acid or dioxane. The first step of reaction 3 is usually carried out with a temperature of about 80° C. (refluxing ethanol), a reaction time of 3–24 hours, a ratio of the amount of compound of formula III to its coreactant of 1:1.3, e.g., in the presence of a protonic solvent, e.g., ethanol. The second step of reaction 3 is usually carried out with a temperature of 80°–120° C., a reaction time of 2–6 hours, a ratio of the amount of compound of step 1 to its coreactant of 1:20, e.g., in a solvent which is the coreactant.

All starting materials are either conventional or readily preparable from known or conventionally preparable starting materials using fully conventional methods, e.g., those disclosed in U.S. Pat. No. 4,280,957; EP No. 27,214A and other references cited herein.

It is well known (Squires, R. F. and Braestrup, C., Nature (London) 266 (1977) 734) that specific sites in the central nervous systems of vertebrates exhibit a high specific affinity for binding 1,4- and 1,5-benzodiazepines. These sites are called benzodiazepine receptors. The pharmacological properties of the compounds of this invention have been investigated by determining their capability for displacing radioactively labelled flunitrazepam from such benzodiazepine receptors.

The compounds of this invention bind more strongly to benzodiazepine receptors than do the known benzodiazepine receptor active compounds. Consequently, the pharmacologically active compounds of this invention have a substantially increased pharmacological activity.

Even if the compounds had no pharmacological effect per se, the increased binding strength would be utilizable to displace other pharmacologically active compounds when such displacement is desired, e.g., to weaken or eliminate their effect.

In any event, in view of their ability to bind benzodiazepine receptors, the compounds are useful to treat diseases of the central nervous system, e.g., insomnia, anxiety, unrest, fear, epilepsy and seizures of various origins, e.g., febrile or toxic. They are particularly useful as tranquilizers in mammals including humans, at daily dosages of 1–200, preferably 1–50 mg/day, using regimens analogous to that used with the conventional tranquilizer Valium.

The pharmacologically active compounds of this invention can be used for the formulation of pharmaceutical preparations, e.g., for oral and parenteral administration to mammals including humans, in accordance with conventional methods of galenic pharmacy.

Conventional excipients include such pharmaceutically acceptable organic or inorganic carrier substances suitable for parenteral or enteral application which do not deleteriously react with the active compounds. Examples of such carriers include water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxiliary agents, such as lubricants, preservatives, stabilizers, wetting agents, emulsifiers, salts for influencing osmotic pressure, buffers and/or coloring substances and the like, which do not deleteriously react with the active compounds.

For parenteral application, particularly suitable are injectable solutions or suspensions, preferably aqueous solutions with the active compound dissolved in polyhydroxyethoxylated castor oil. Ampoules are convenient unit dosages.

For oral application, particularly suitable are tablets, dragees, or capsules having talc and/or a carbohydrate carrier or binder or the like, the carrier preferably being lactose and/or corn starch and/or potato starch. A syrup, elixir or the like can be used wherein a sweetened vehicle can be employed.

Generally, the compounds of this invention are dispensed in unit dosage form comprising 0.05–100 mg in a pharmaceutically acceptable carrier per unit dosage.

The dosage of the compounds according to this invention for treatment of all of the above indications is 0.1–300 mg/day, preferably 1–30 mg/day, when administered to patients, e.g., humans, as a drug. Suitable dosages and regimens for a given host can be determined, using conventional considerations, e.g., by customary comparison of the differential activities of the subject compound and of a known agent, e.g., by means of an appropriate, conventional pharmacological protocol.

The flunitrazepam displacement activity of the compounds of this invention has been determined by determining the $IC_{50}$ (ng/ml) value and $ED_{50}$ value.

The $IC_{50}$ value represents the concentration which causes a displacement of 50% of the specific binding of $^3H$-flunitrazepam (1.0 nM, 0° C.) in samples comprising a total volume of 0.55 ml of a suspension of brain membrane, e.g., from rats.

The displacement test is performed as follows: 0.50 ml of a suspension of non-treated rat forebrain in 25 mM $KH_2PO_4$, pH=7.1 (5–10 mg tissue/sample) is incubated for 40–60 minutes at 0° C. together with $^3H$-diazepam (specific activity 87 Ci/mmol, 1.0 nM) or $^3H$-flunitrazepam (specific activity 87 Ci/mmol, 1.0 nM). After incubation, the suspension is filtered through "Whatman GF/C" glass fiber filters, the residue washed twice with cold buffer solution and the radioactivity measured by scintillation counting.

The test is repeated, except that prior to the addition of the radioactively labelled benzodiazepine, a given amount or an excess amount of the compound, the displace capability of which is to be determined, is added. Based on the data obtained the $IC_{50}$ value can be calculated.

The $ED_{50}$ value represents the dose (mg/kg) of a test substance which causes the specific binding of flunitrazepam to benzodiazepine receptors in a living brain to be reduced to 50% of the control value. Such an in vivo test is carried out as follows:

Groups of mice are injected with the test substance at different doses and usually subcutaneously. 15 minutes later, $^3H$-flunitrazepam is given intravenously to the mice and after a further 20 minutes, the mice are killed, their forebrain membrane is quantified by scintillation counting. The $ED_{50}$ value is determined from dose-response curves.

Test results obtained by testing some of the compounds of this invention and some well known benzodiazepine receptor active compounds are shown in TABLE 1.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

TABLE 1

| Test substance | Inhibition of $^3H$—flunitrazepam-binding | |
|---|---|---|
| | in vitro $IC_{50}$ ng/ml | in vivo $ED_{50}$ mg/kg |
| 3-[5-(3-ethyl-1,2,4-oxadiazole)-yl]-5,6-dihydro-5-methyl-6-oxo-4H— imidazo[1,5-a][1,4]benzodiazepine | 12 | 2.2 |

TABLE 1-continued

| Test substance | Inhibition of $^3H$—flunitrazepam-binding | |
|---|---|---|
| | in vitro $IC_{50}$ ng/ml | in vivo $ED_{50}$ mg/kg |
| 8-chloro-5,6-dihydro-3-[5-(3-ethyl-1,2,4-oxadiazole)-yl]-5-methyl-6-oxo-4H—imidazo[1,5-a][1,4]benzodiazepine | >10 | 5.9 |
| 5,6-dihydro-3-[5-(3-ethyl-1,2,4-oxadiazole)-yl]-8-fluoro-5-methyl-6-oxo-4H—imidazo[1,5-a][1,4]benzodiazepine | 3.5 | 4.5 |
| ethyl-5,6-dihydro-5-methyl-6-oxo-4H—imidazo[1,5-a][1,4]benzodiazepine-3-carboxylate* | | >30 |
| ethyl-8-chloro-5,6-dihydro-5-methyl-6-oxo-4H—imidazo[1,5-a][1,4]benzodiazepine-3-carboxylate* | 7.9 | >30 |
| ethyl-5,6-dihydro-8-fluoro-5-methyl-6-oxo-4H—imidazo[1,5-a][1,4]benzodiazepine-3-carboxylate* | | 4 |

*See EP 27,214A

EXAMPLE 1

3-[5-(3-ethyl-1,2,4-oxadiazole)-yl]-5,6-dihydro-5-methyl-6-oxo-4H-imidazo[1,5-a][1,4]benzodiazepine A: 5,6-dihydro-5-methyl-6-oxo-4H-imidazo[1,5-a][1,4]benzodiazepine-3-carboxylic acid imidazolide A solution of 1.8 ml thionyl chloride in 25 ml of dry tetrahydrofuran (THF) was added dropwise to a solution of 6.8 g imidazole in 75 ml dry THF. After stirring for 1 hour, the reaction mixture was filtered and the filtrate was added dropwise to 0.0125 mole of dry 5,6-dihydro-5-methyl-6-oxo-4H-imidazo[1,5-a][1,4]benzodiazepine-3-carboxylic acid in 100 ml dry dimethyl formamide. The reaction mixture was left overnight at room temperature with exclusion of water.

In a similar manner the following compounds were prepared:

a. 8-chloro-5,6-dihydro-5-methyl-6-oxo-4H-imidazo[1,5-a][1,4]benzodiazepine-3-carboxylic acid imidazolide.

b. 5,6-dihydro-8-fluoro-5-methyl-6-oxo-4H-imidazo[1,5-a][1,4]-benzodiazepine-3-carboxylic acid imidazolide.

c. 1-methyl-8-nitro-6-phenyl-4H-imidazo[1,5-a][1,4]benzodiazepine-3-carboxylic acid imidazolide.

d. 7-chloro-5,6-dihydro-5-methyl-6-oxo-4-imidazo[1,5-a][1,4]benzodiazepine-3-carboxylic acid imidazolide.

B: Propionamide oxime

A solution of 2.3 g of sodium in 40 ml of methanol was added dropwise to a solution of 6.9 g hydroxylamine hydrochloride in 100 ml methanol. The reaction mixture was left for one hour before it was filtered. 0.11 mole propionitrile was added dropwise to the filtrate, and the reaction mixture was allowed to stand for 2 days at room temperature with exclusion of water.

In a similar manner solutions of the following compounds were prepared.

| acetamide oxime | from acetonitrile |
|---|---|
| bytyramide oxime | from butyronitrile |

C: 3-[5-(3-ethyl-1,2,4-oxadiazole)-yl]-5,6-dihydro-5-methyl-6-oxo-4H-imidazo[1,5-a][1,4]benzodiazepine The solution of propionamide oxime in methanol was concentrated in vacuo and after addition of toluene the solvent was evaporated again. The residue was heated for 5 minutes in a steam bath, and an exothermal reaction took place. After termination of the reaction the solution of 5,6-dihydro-5-methyl-6-oxo-4H-imidazo[1,5-a][1,4]benzodiazepine-3-carboxylic acid imidazolide in THF-DMF was added. The next day the solution was concentrated in vacuo, and 200 ml toluene was added. This mixture was refluxed for 3 hours. The hot mixture was then filtered and the filtrate evaporated. The yield was 1.2 g of 3-[5-(3-ethyl-1,2,4-oxadiazole)-yl]-5,6-dihydro-5-methyl-6-oxo-4H-imidazo[1,5-a][1,4]benzodiazepine with a melting point of 182°–4° C.

In a similar way, by combination of different carboxylic imidazolides with different amide oximes the following compounds were prepared:
8-chloro-5,6-dihydro-3-[5-(3-ethyl-1,2,4-oxadiazole)-yl]-5-methyl-6-oxo-4H-imidazo[1,5-a][1,4]benzodiazepine, m.p. 169°–74° C.
5,6-dihydro-3-[5-(3-ethyl-1,2,4-oxadiazole)-yl]-8-fluoro-5-methyl-6-oxo-4H-imidazo[1,5-a][1,4]benzodiazepine, m.p. 185°–94° C.
1-methyl-8-nitro-6-phenyl-3-[5-(3-propyl-1,2,4-oxadiazole)-yl]-4H-imidazo-[1,5-a][1,4]benzodiazepine, m.p. 211°–9° C.
7-chloro-5,6-dihydro-3-[5-(3-ethyl-1,2,4-oxadiazole)-yl]-5-methyl-6-oxo-4H-imidazo[1,5-a][1,4]benzodiazepine, m.p. 171°–178° C.

EXAMPLE 2

8-chloro-6-(2-chlorophenyl)-3-[5-(3-methyl-1,2,4-oxadiazole)-yl]-4H-imidazo[1,5-a][1,4]benzodiazepine A: 8-chloro-6-(2-chlorophenyl)-N[(dimethylamino)ethylidene]-4H-imidazo[1,5-a][1,4]benzodiazepine-3-carboxamide A mixture of 0.0047 mole 8-chloro-6-(2-chlorophenyl)-4H-imidazo[1,5-a][1,4]benzodiazepine-3-carboxamide and 3 ml of dimethyl acetamide dimethyl acetate was heated in an oil bath at a temperature of about 115° C. After cooling the crystals were collected on a glass filter and washed with dimethyl formamide (DMF) and ether.

B. 8-chloro-6-(2-chlorophenyl)-3-[5-(3-methyl-1,2,4-oxadiazole)-yl]-4H-imidazo[1,5-a][1,4]benzodiazepine A mixture of 1.3 ml of water, 1.3 ml of 4M sodium hydroxide, 7 ml of glacial acid, 5 ml of dioxane, 0.35 g of hydroxylamine hydrochloride and 0.0037 mole of 8-chloro-6-(2-chlorophenyl)-N[(dimethylamino)ethylidene]-4H-imidazo[1,5-a][1,4]benzodiazepine-3-carboxamide was heated to 90° C. for 2 hours. After cooling and addition of 20 ml of water, the solid product was collected on a glass filter and was washed with 40 ml of water.

The yield was 0.75 g, m.p. 174°–82° C.

EXAMPLE 3

3-[3-(5-ethyl-1,2,4-oxadiazole)-yl]-5,6-dihydro-5-methyl-6-oxo-4H-imidazo[1,5-a][1,4]benzodiazepine A: 5,6-dihydro-5-methyl-6-oxo-4H-imidazo[1,5-a][1,4]benzodiazepine-3-carboxamide oxime A mixture of 0.0125 mole 3-cyano-5,6-dihydro-5-methyl-6-oxo-4H-imidazo[1,5-a][1,4]benzodiazepine, 1.1 g of hydroxylamine hydrochloride, 200 ml of 99% ethanol and 5.2 ml of a 20% potassium carbonate solution in water was refluxed for 22 hours. The reaction mixture was filtered and the filtrate was concentrated. The residue was treated with 100 ml of water and the crystalline solid was filtered off and was washed with water.

B. 3-[3-(5-ethyl-1,2,4-oxadiazole)-yl]-5,6-dihydro-5-methyl-6-oxo-4H-imidazo[1,5-a][1,4]benzodiazepine A mixture of 0.0056 mole of 5,6-dihydro-5-methyl-6-oxo-4H-imidazo-[1,5-a][1,4]benzodiazepine-3-carboxamide oxime and 10 ml of propionic acid anhydride was stirred for 2 hours at 20° C. and thereafter for 5 hours at 120° C. After evaporation 100 ml of THF was added and the mixture was saturated with gaseous methylamine. The reaction mixture was allowed to stand overnight at room temperature whereafter the mixture was concentrated in vacuo. 100 ml methylene chloride was added and the mixture was filtered. The filtrate was concentrated and treated with 10 ml of ethyl acetate.

The yield was 0.0015 mole; m.p. 167°–74° C.

The starting materials for preparation of the compounds of Examples 1 to 3 are readily prepared by using methods known in the art. See for example U.S. Pat. No. 4,280,957; and EP published patent application No. 27,214, whose disclosures are incorporated by reference herein.

Oxadiazoles and other heterocyclic substituted derivatives of heterocyclic fused benzodiazepines are mentioned in DE published patent application No. 2,242,918, although none of the hetero aromatic derivatives of this invention are synthesized.

The preceding examples can be repeated with similar success by substituting the generically or specifically described reactants and/or operating conditions of this invention for those used in the preceding examples. From the foregoing description, one skilled in the art can easily ascertain the essential characteristics of this invention and without departing from the spirit and scope thereof make various changes and modifications of the invention to adapt it to various usages and conditions.

What is claimed is:

1. An oxadiazolyl-imidazo-[1,4]benzodiazepine of the formula

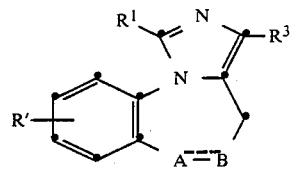

wherein,
R' is hydrogen or chlorine, fluorine or nitro in the 7- or 8-position,
R¹ is hydrogen or alkyl of 1-3 carbon atoms,
R³ is an oxadiazolyl of the formula

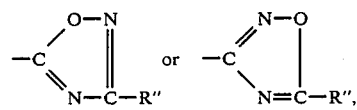

R" is alkyl of 1-3 carbon atoms,
A ═ B is

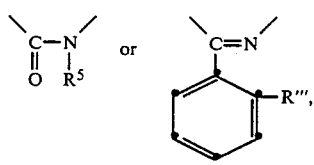

R[5] is hydrogen or methyl, and
R''' is hydrogen or chlorine.

2. 3-[5-(3-Ethyl-1,2,4-oxadiazole)-yl]-5,6-dihydro-5-methyl-6-oxo-4H-imidazo[1,5-a][1,4]benzodiazepine, a compound of claim 1.

3. 8-Chloro-5,6-dihydro-3-[5-(3-ethyl-1,2,4-oxadiazole)-yl]-5-methyl-6-oxo-4H-imidazo[1,5-a][1,4]benzodiazepine, a compound of claim 1.

4. 5,6-Dihydro-3-[5-(3-ethyl-1,2,4-oxadiazole)-yl]-8-fluoro-5-methyl-6-oxo-4H-imidazo[1,5-a][1,4]benzodiazepine, a compound of claim 1.

5. 1-Methyl-8-nitro-6-phenyl-3-[5-(3-propyl-1,2,4-oxadiazole)-yl]-4H-imidazo[1,5-a][1,4]benzodiazepine, a compound of claim 1.

6. 8-Chloro-6-(2-chlorophenyl)-3-[5-(3-methyl-1,2,4-oxadiazole)-yl]-4H-imidazo[1,5-a][1,4]benzodiazepine, a compound of claim 1.

7. 3-[3-(5-Ethyl-1,2,4-oxadiazole)-yl]-5,6-dihydro-5-methyl-6-oxo-4H-imidazo[1,5-a][1,4]benzodiazepine, a compound of claim 1.

8. 7-Chloro-5,6-dihydro-3-[5-(3-ethyl-1,2,4-oxadiazole)-yl]-5-methyl-6-oxo-4H-imidazo[1,5-a][1,4]benzodiazepine, a compound of claim 1.

9. A compound of claim 1 wherein R[3] is

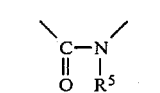

10. A compound of claim 1 wherein A ≡ B is

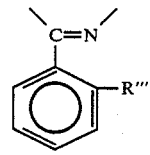

11. A compound of claim 1 wherein A ≡ B is

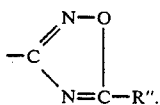

12. A compound of claim 1 wherein R[3] is

-C⟨N-O, N=C-R''⟩.

13. A compound of claim 1 wherein R' is 8-Cl, 8-F or 8-NO$_2$.

14. A compound of claim 1 wherein R' is 7-Cl, 7-F or 7-NO$_2$.

15. A pharmaceutical composition comprising an amount of a compound of claim 1 effective as a therapeutic agent for the treatment of a disease of the central nervous system, and a pharmaceutically acceptable carrier.

16. A method of treating a patient suffering from a disease of the central nervous system which comprises administering to the patient an amount of a compound of claim 1 effective as a therapeutic agent for the treatment of the disease of the central nervous system.

* * * * *